United States Patent [19]
Conti et al.

[11] Patent Number: 5,879,661
[45] Date of Patent: Mar. 9, 1999

[54] IMAGING AGENTS AND METHODS FOR THE PREPARATION AND USE THEREOF

[75] Inventors: Peter S. Conti, Pasadena; Mian M. Alauddin, Alhambra; John D. Fissekis, South Pasadena, all of Calif.

[73] Assignee: University Advanced Bio-Imaging Associates, Los Angeles, Calif.

[21] Appl. No.: 518,407

[22] Filed: Aug. 23, 1995

[51] Int. Cl.$^6$ .......................... A61K 51/00; A61M 36/14
[52] U.S. Cl. ........................ 424/1.81; 424/1.11; 424/1.65
[58] Field of Search .................. 424/1.11, 1.65, 424/1.73, 1.81, 9.1, 9.3, 9.4, 9.5

[56] References Cited

U.S. PATENT DOCUMENTS

| | | | |
|---|---|---|---|
| 4,489,052 | 12/1984 | Price | 424/1.11 |
| 5,703,056 | 12/1997 | Blasberg et al. | 514/44 |

OTHER PUBLICATIONS

Saito et al. (1984), Annals of Neurology, vol. 15, No. 6, pp. 548–558 Diagnostic imaging of herpes simplex virus encephalitis using a radiolabeled antiviral drug: autoradiographic assessment in an animal model (abstract).

Watanabe (1979), J. Med. Chem., vol. 22, No. 1, pp. 21–24, "Nucleosides. 110. Synthesis and Antiherpes Virus Activity of Some 2'–fluoro–2'–deoxyarabinofuranoryl–pyrimidine Nucleosides".

Saito et al (1982). Science, vol. 217, pp. 1151–1153, "Quantitative Auto Radiographic Mapping of Herpes Simplex Virus Encephalitis with a Radiolabeled Antiviral Drug".

Alauddin et al (1994), 208th Meeting of the American Chemical Society, Washington, D.C., Aug. 21–24, "Synthesis of 2'–fluoro–5–["C–methyl 1]–1–β–arabino–furanosyluracil (["C ]–FMAU) for use in vivo imaging by position emission tomography." (Abstract).

Conti et al (Aug. 1995), Nucl. Med. Biol., vol. 22, No. 6, pp. 783–789, Synthesis of 2'–fluoro–5–["C]–methyl–1–β–D–Arabinofuranosyluracil(["C]–FMAU): A Potential Nucleoside Analog for In Vivo Study of Cellular Proliferation with PET.

Matulic–Adamic et al (1988), J. Med. Chem., vol. 31, pp. 1642–1647, "Nucleosides. 150. Synthesis and Some Biological Properties of 5–mono–fluoromethyl, 5–difluoromethyl, and 5–trifluromethyl derivatives of 2'–deoxyuridine and 2'deoxy–2'–fluoro–β–D–arabino furanosylurocil".

*Primary Examiner*—Jose'G. Dees
*Assistant Examiner*—Dameron Jones
*Attorney, Agent, or Firm*—Fulbright & Jaworski L.L.P.

[57] ABSTRACT

The nucleoside analog 2'-fluoro-5-methyl-1-β-D-arabinofuranosyluracil (FMAU) has been found to have an especially desirable combination of properties for use as an imaging agent, including in particular limited in vivo catabolism. Methods for the preparation of the [$^{11}$C]-labelled FMAU and for the use of the labelled material are also provided.

6 Claims, 1 Drawing Sheet

IMAGING AGENTS AND METHODS FOR THE PREPARATION AND USE THEREOF

BACKGROUND OF THE INVENTION

This invention relates generally to the fields of biochemistry and medicine. More particularly, the present invention relates to compositions for use in imaging cancer or infectious disease.

Imaging of cellular proliferation in vivo using radiolabeled analogues of nucleosides such as [$^{131}$I]-IUdR and [$^{11}$C]-thymidine is plagued by extensive catabolism of the parent compounds following intravenous administration, limiting uptake into the DNA of tumor tissues. Such catabolic events include dehalogenation, cleavage of the sugar moieties from the base, and ring opening of the base. In vivo assessment of such events requires complex mathematical models to interpret kinetic data obtained in imaging studies.

Mathematical models currently being designed to interpret positron emission tomography (PET) kinetic data obtained from [$^{11}$C] thymidine studies in tumors are generally cumbersome, in large measure due to the presence of significant levels of short-term catabolism of thymidine with subsequent production of several radiolabeled byproducts in plasma and tissue [Martiat P. H., Ferrant A., Labar D., et al. (1988) In vivo measurement of carbon-11 thymidine uptake in non-Hodgkin's lymphoma using positron emission tomography. *J. Nucl. Med.* 29, 1633–1637; Shields A. F., Larson S. M., Grunbaum A., and Graham M. M. (1984). Short-term thymidine uptake in normal and neoplastic tissues: Studies for PET. *J. Nucl. Med.* 25, 759–764; Shields A. F., Coonrod D. U., Quakenbush R. C., et al. (1987) Cellular sources of thymidine nucleotides: Studies for PET. *J. Nucl. Med.* 28, 1435–1440; Wong C. Y. O., Yue N., Chan B., et al. (1994) [$^{11}$C]-Thymidine PET imaging as a measure of DNA synthesis rate: A preliminary quantitative study of human brain glioblastoma. *J. Nucl. Med.* 35, 9P; Mankoff D. A., Graham M. M., and Shields A. F. (1994a) Graphical analysis method for estimating blood-to-tissue transfer constants for tracers with labeled metabolites. *J. Nucl. Med.* 35, 34P, 1994; Mankoff D. A., Shields A. F., Lee T. T., and Graham M. M. (1994b) Tracer kinetic model to quantitative imaging of thymidine utilization using [$^{11}$C]-thymidine and PET. *J. Nucl. Med.* 35, 138P]. Though potentially less complex, modeling of the kinetic behavior of ring labeled thymidine is likewise non-trivial [Shields ASF., Graham M. M., and O'Sullivan F. (1992) Use of [$^{11}$C]-thymidine with PET and kinetic modeling to produce images of DNA synthesis. *J. Nucl. Med.* 33, 1009–1010; Mankoff et al., 1994a,b, supra]. In the case of imaging studies with radioiodinated IUdR using conventional nuclear medicine techniques, in addition to significant dehalogenation it has also been demonstrated that UdR, once formed, may be converted to TdR in mammalian systems and subsequently incorporated into DNA [Commerford S. L. and Joel D. D. (1979) Iododeoxyuridine administered to mice is de-iodinated and incorporated into DNA primarily as thymidylate. *Biochem. Biophys. Res. Comm.* 86, 112–118].

The short-term catabolism of [$^{11}$C and $^{14}$C-methyl]-thymidine have been extensively studied [Conti P. S., Hilton J., Magee C. A., and Anderson J. H. (1989) Tumor imaging with positron-emission tomography (PET) and [$^{11}$C]-thymidine: Determination of radiolabeled thymidine metabolites by high pressure liquid chromatography (HPLC) for kinetic data analysis. *Radiology* 173, P402; Conti P. S., Hilton J., Magee C. A., and Anderson J. H. (1990) Analysis of nucleoside metabolism during positron emission tomography (PET) imaging studies of brain tumors with carbon-11 labeled thymidine (TdR). 199*th Meeting of American Chemical Society*, Boston, Mass. April 22–27]. Such studies have demonstrated that significant catabolism occurs once thymidine has been administered intravenously, with the notable radiolabeled products being thymine, dihydrothymine, beta-ureidoisobutyric acid, and beta-aminoisobutyric acid. The latter constitutes the most abundant radiolabeled species in plasma and tissues by 10 minutes post-injection. While [$^{11}$C]-$CO_2$ is the most abundant radiolabeled species in plasma following administration of ring labeled thymidine [Shields A. F., Kozell L. B., Link J. M., et al. (1990b) Comparison of PET imaging using [$^{11}$C]-thymidine labeled in the ring-2 and methyl positions. *J. Nucl. Med.* 31, 794; Shields A. F., Swenson E. R., and Bassingthwaighte J. B. (1990c) Contribution of labeled carbon dioxide to PET imaging of [$^{11}$C]-labeled compounds. *J. Nucl. Med.* 31, 909], radiolabeled thymine, dihydrothymine, and beta-ureidoisobutyric acid also are present, albeit in lesser amounts. Despite its extensive catabolism, it has been demonstrated that [$^{11}$C]-thymidine has utility in tumor imaging in both animal models and patients [Larson S. M., Weiden P. L., Grunbaum A., et al. (1981) Positron imaging feasibility studies. I: Characteristics of [$^3$H]-thymidine uptake in rodent and canine neoplasms: Concise Communication. *J. Nucl. Med.* 22, 869–874; Conti P. S., Kleinert E. L., Schmall B., et al. (1984a) Potential use of carbon-11 labeled thymidine (TdR) for studying the effect of therapy on prostatic adenocarcinoma in vivo. 32*nd Annual Meeting of the Radiation Research Society*, Orlando, Fla., March 25–29; Conti P. S., Kleinert E. L., Schmall B., Whitmore W. F., Jr. (1984b) Comparative uptake studies of radiolabeled thymidine in the Dunning R3327H fast-growing and R3327H slow-growing prostate adenocarcinomas in vivo. 79*th Meeting of the American Urological Association*, New Orleans, La., May 6–10; Conti, P. S., Schmall, B., Herr, H. W., et al. (1985) Carbon-11 labeled alpha-aminoisobutyric acid, 2-deoxy-D-glucose and thymidine as potential imaging agents for prostatic and renal malignancies. *Surgical Forum* 36, 635–637; Conti P. S., Camargo E. E., Grossman S. A., et al. (1991) Multiple radiotracers for evaluation of intracranial mass lesions using PET. *J. Nucl. Med.* 32, 954; Shields et al., 1984, 1987, 1990b,c, supra; Shields A. F., Lim K., Grierson J., et al. (1990a) Utilization of labeled thymidine in DNA synthesis: Studies for PET. *J. Nucl. Med.* 31, 337–342; Martiat et al. 1988, supra; Strauss L. G. and Conti P. S. (1991) The applications of PET in clinical oncology. *J. Nucl. Med.* 32, 623–648; Schmall B., Conti P. S., Schaeffer D. J., and Kleinert E. L. (1992) Tumor and organ biochemical profiles determined in vivo following uptake of a combination of radiolabeled substrates: Potential applications for PET. *Amer. J Phys. Imag.* 7, 2–11; Wong et al. 1994, supra; Vander Borght T., Pauwels S., Lambotte L., et al. (1994) Brain tumor imaging with PET and 2-[$^{11}$C]-thymidine. *J. Nucl. Med.* 35: 974–982].

There is thus a long-felt need in the art for a suitable partially or non-catabolized imaging agent (e.g., nucleoside analog) for use in, e.g., tumor proliferation studies with PET. Except for limited catabolism, an ideal tracer should share the other in vivo characteristics of thymidine, including cell transport, phosphorylation by mammalian kinase, and incorporation into DNA. In particular, development of a partially or non-catabolized thymidine analog would greatly simplify imaging and modeling approaches and potentially provide higher tumor to target ratios due to more selective incorporation of radiotracer.

It is an object of the present invention to provide compositions and methods which do not suffer from the drawbacks of the heretofore-known compositions.

SUMMARY OF THE INVENTION

Pursuant to the present invention, the nucleoside analog 2'-fluoro-5-methyl-1-β-D-arabinofuranosyluracil (FMAU) has been found to have an especially desirable combination of properties for use as an imaging agent, including in particular limited in vivo catabolism. Methods for the preparation of the [$^{11}$C]-labelled FMAU and for the use of the labelled material are also provided.

BRIEF DESCRIPTION OF THE DRAWINGS

These and other features, aspects, and advantages of the present invention will become better understood iwth regard to the following description, appended claims, and accompanying drawing where:

DETAILED DESCRIPTION OF THE INVENTION

Figure 1:
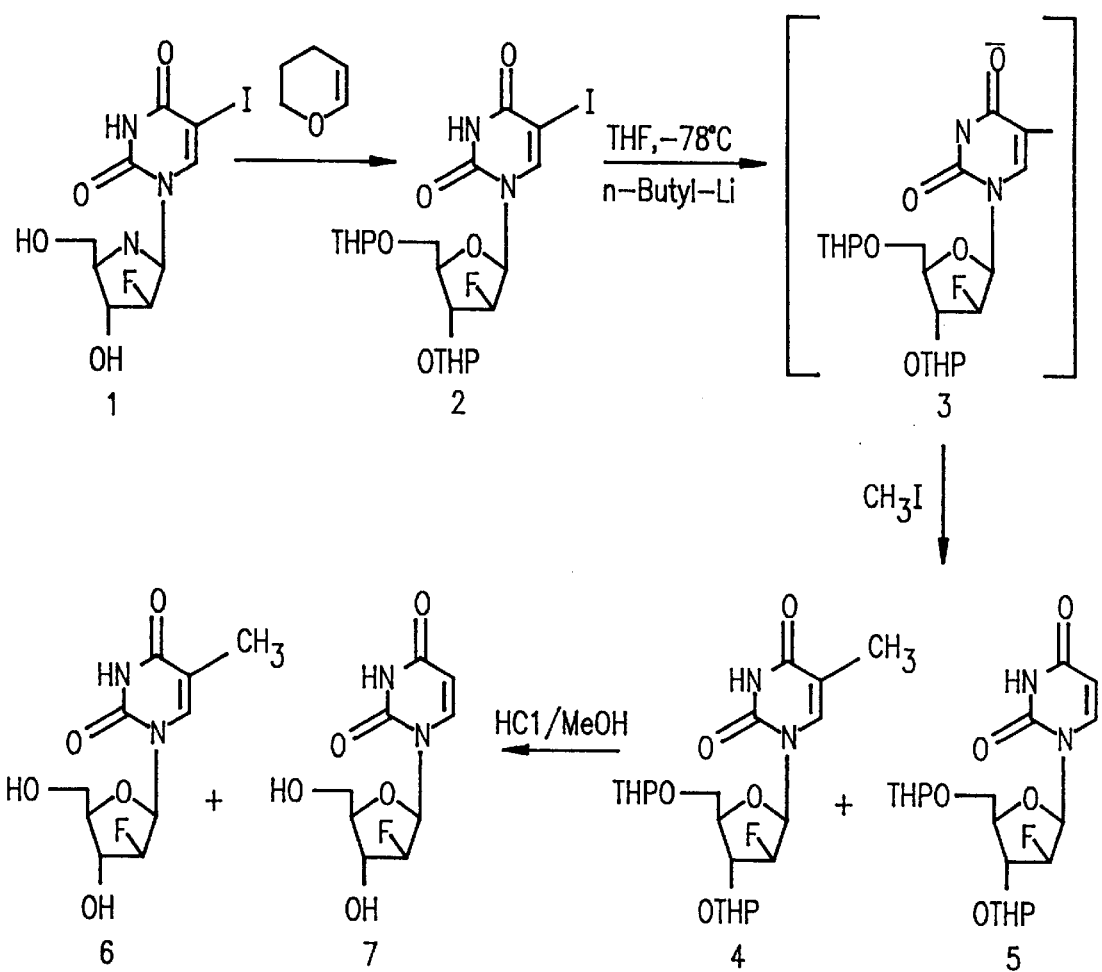
FIG. 1 illustrates the synthesis of FMAU.

Over the last decade, much research has been directed to exploring the radiosynthesis and in vivo pharmacology of antiviral and antileukemic nucleoside derivatives, including agents such as [$^{125}$I] 2'-fluoro-5-iodo-1-β-D-arabinofuranosyl-cytosine (FIAC) [Perlman M. F., Conti P. S., Schmall B., and Watanabe K. A. (1984) Synthesis and purification of the antiviral agent 1-(2-deoxy-2-fluoro-β-D-arabinofuranosyl)-5-iodocytosine (FIAC) labeled with iodine-125. *Int. J. Nucl. Med. Biol.* 11, 215–218], [$^{125}$I, $^{131}$I, $^{123}$I] 2'-fluoro-5-iodo-1-β-D-arabinofuranosyl-uracils (FIAU) [Misra H K, Knaus E E, Wiebe L I, and Tyrrell D L. (1986) Synthesis of [$^{131}$I, $^{125}$I, $^{123}$I and $^{82}$Br]-labelled 5-halo-1-(2-Deoxy-2-fluoro-β-D-arabinofuranosyl)uracils. *Appl Radiat Isot* 37, 901–905], [$^{11}$C-N-methyl] acyclovir [Wilson A. A., Conti P. S., Dannals R. F., et al. (1991) Radiosynthesis of [$^{11}$C]-N-methylacyclovir. *J. Lab. Compd. Radiopharm.* 29, 765–768], and a [$^{18}$F] derivative of 9-[(1, 3-dihydroxy-2-propoxy)methyl] guanine (DHPG) [Alauddin M. M., Conti P. S., Mazza S. M., et al. (1993a) A novel synthesis suitable for labeling the antiviral agent 9-[(3-fluoro-1-hydroxy-2-propoxy)methyl] guanine (FHPG) with [$^{18}$F] for in vivo imaging by positron emission tomography. *206th Meeting of the American Chemical Society*, Chicago, Ill., August 22–26]. Synthesis of 2'-fluoro-5-[$^{11}$C-methyl]-1-β-D-arabinofuranosyluracil ([$^{11}$C]-FMAU) for use in in vivo imaging by positron emission tomography. *208th Meeting of the American Chemical Society*, Washington D.C., August 21–24]. Although some of these agents have potential utility in imaging cancer and/or infectious diseases, many undergo some form of catabolism leading to either loss of radiolabel or formation of multiple radiolabeled by-products. For example, administration of [$^{125}$I] labeled FIAC results in extensive deiodination in vivo [Perlman et al., 1984, supra]. In addition, FIAU can be formed in vivo from deamination of administered FIAC [Chou T-C, Feinberg A, Grant A J, et al. (1981) Pharmacological disposition and metabolic fate of 2'-fluoro-5-iodo-1-β-D-arabinofuranosyl-cytosine in mice and rats. *Cancer Res.* 41, 3336–3342; Grant A. J., Feinberg A., Chou T-C, et al. (1982) Incorporation of metabolites of 2'-fluoro-5-iodo-1-β-D-arabinofuranosylcytosine into deoxyribonucleic acid of neoplastic and normal mammalian tissues. *Biochem. Pharn.* 31, 1103–1108]. A similar situation to IUdR also exists during the metabolism of -FIAU. Although FIAU is less likely than IUdR to be catabolized by enzymatic cleavage of the glycosyl-base bond due to reasons discussed below, and can itself be incorporated into DNA, deiodination followed by methylation at the 5 position of the base also can occur prior to DNA incorporation [Chou et al., 1981, supra; Grant et al., 1982, supra].

Pursuant to the present invention, the antiviral and antileukemic agent, 2'-fluoro-5-methyl-1-β-D-arabinofuranosyluracil (FMAU) is demonstrated to be ideally suited as an in vivo radiotracer of cellular proliferation without the presence of complicated catabolism. FMAU has been shown to be phosphorylated by both mammalian and viral kinases, serving as a good substrate relative to thymidine in cell culture systems [Chou T-C., Kong X-B., Fanucchi M. P., et al. (1987) Synthesis and biological effects of 2'-fluoro-5-ethyl-1-β-D-arabinofuranosyluracil. *Antimicrob. Agents Chemother.* 31, 1355–1358; Fox J. J., Watanabe K. A., Chou T-C., et al. (1987) Antiviral activities of 2'-fluorinated arabinosyl-pyrimidine nucleosides. In: *Fluorinated Carbohydrates* (Ed. N. F. Taylor, American Chemical Society, Washington, D.C.) Chapter 10, pp. 176–190]. FMAU is transported into cells and phosphorylated by mammalian kinases to levels approaching that of thymidine, displaying substantial incorporation of [2-$^{14}$C]-FMAU into host DNA, and an ED$_{50}$ of 8–28 μM for inhibition of thymidine incorporation [Chou et al., 1987, supra]. Accumulation of [2$^{14}$C]-FMA J has also been preferentially observed in organs with rapidly dividing cells such as the small intestine and spleen of rats, as well as in proliferating PC12 and Vero cells in culture [Saito Y., Rubenstein R., Price R. W., et. al. (1984) Diagnostic imaging of herpes simplex virus encephalitis using a radiolabeled antiviral drug: autoradiographic assessment in an animal model. *Ann. Neurol.* 15, }548–558].

Nearly all injected radioactivity of intravenously administered [$^{14}$C]-FMAU into mice, rats and dogs is cleared into the urine [Philips F. S., Feinberg A., Chou T-C., et al. (1983) Distribution, metabolism, and excretion of 1-(2-fluoro-2-deoxy-β-D-arabinofuranosyl)thymine and 1-(2-fluoro-2-deoxy-β-D-arabinofuranosyl)-5-iodocytosine. *Cancer Res* 43, 3619–3627]. In all three species, urine radioactivity through 24 hours is composed primarily of unchanged parent compound as determined by HPLC following intravenous administration of [2-$^4$G]-FMAU [Philips et al., 1983, supra]. Four minor metabolites have been detected in mouse, rat, and dog urine at 24 hr accounting for less than 3% (dogs), 5% (rats) and 15% (mice) of total urine radioactivity. One metabolite has been identified as the 5-hydroxymethyl derivative of FMAU [Philips et al., 1983, supra; Feinberg A., Vidal P., Fox J. J., et al. (1983) 2'-Fluoro-5-methyl-1-β-D-arabinosyluracil (FMAU), a potent antiviral agent is metabolized in mice to 2'-fluoro-5-hydroxymethyl-1-β-D-arabinosyluracil and to an FMAU adduct. *Proc. Amer. Assoc. Cancer Res.* } *p46*]. Of these trace metabolites, a glucuronide adduct of FMAU, while present in all three species, appears to be most abundant in dogs [Philips et al., 1983, supra; Feinberg et al., 1983, supra; Feinberg A., Vidal P.M., Fox J. J., et al. (1984) Structures of metabolites isolated from urine of mice treated with the antiviral agent, 1-(2'-deoxy-2'-fluoro-1-β-D-arabinofuranosyl)-5-methyluracil. *Drug Metab. Disp.* 12, 784–786].

Ab initio studies using quantum-chemical methods have been used to explain the lack of significant catabolism of this compound, as well as its ability to be phosphorylated and incorporated into DNA. These studies have suggested that the fluorine atom in the sugar moiety locks the sugar-base bond in the anti conformation [Sapse A. M. and Snyder G.

(1985) Ab initio studies of the antiviral drug 1-(2-fluoro-2-deoxy-β-D-arabinofuranosyl)thymine. *Cancer Invest.* 3, 115–121]. While the fluorine atom is similar enough to hydrogen, with respect to van der Waals radii, to allow action by the polymerase leading to incorporation into DNA, it is suggested that it is large enough also to sterically hinder the rotation of the base around the sugar-base bond. Likewise, the locked anti-conformation probably enhances exposure to the DNA polymerase. Resistance to cleavage of the glycosyl bond by phosphorylase may be secondary to the electrostatic attraction of the fluorine atom on the $C_2'$ to the positive guanidinium group of an arginine responsible for bond cleavage at the active site of the enzyme. The ribo-isomer, on the other hand, exhibits a 1000-fold diminished biological activity.

Two Phase I trials to evaluate the clinical efficacy of FMAU as an antineoplastic agent have been conducted [Abbruzzese J. L., Schmidt S., Raber M. N., Levy J K, et al. (1989) Phase I trial of 1-(2'-deoxy-2'-fluoro-1-β-D-arabinofuranosyl)-5-methyluracil (FMAU) terminated by severe neurologic toxicity. *Invest. New Drugs* 7, 195–201; Fanucchi M. P., Leyland-Jones B., Young C. W., et al. (1985) Phase I trial of 1-(2'-deoxy-2'-fluoro-1-β-D-arabinofuranosyl)-5-methyluracil (FMAU). *Cancer Treat. Rep.* 69, 55–59]. Significant dose-limiting neurotoxicity developed in patients treated with doses above 8 mg/m$^2$×5 days [Abbruzzese et al., 1989, supra]. Preclinical toxicology studies in dogs previously demonstrated an $LD_{10}$ of 25 mg/m$^2$×10 days [Fannuchi et al., 1985, supra].

In production of [$^{11}$C]-FMAU prepared in accordance with the present invention, specific activities achieved range from 50–100 Ci/mmol. Between 50–100 μg of unlabeled FMAU would be administered intravenously into humans using 20 mCi doses of material with this specific activity, although somewhat larger or smaller doses may be appropriate in particular instances, as would be appreciated by those working in the field. This is approximately 1000-fold less than the minimum therapeutic dose noted to cause significant side effects in patients [Abbruzzese et al., 1989, supra; Fannuchi et al., 1985, supra]. Administration of the agents and their use in imaging (for example, using positron emission tomography) would be routine for those skilled in the imaging art.

The synthesis of [$^{11}$C-methyl]-FMAU described herein was based broadly on a previously developed procedure for [$^{11}$C-methyl]-thymidine [Sundoro-Wu B. M., Schmall B., Conti P. S. et al. (1984a) Selective alkylation of pyrimidyl-dianions: Synthesis and HPLC of carbon-11 labeled thymidine for tumor visualization using positron emission tomography. *Int. J Appl. Radiat. Isot.* 35, 705–708; Sundoro-Wu B. M., Schmall B., Conti P. S., and Watanabe K. A. (1984b) Selective alkylation suitable for labeling the antiviral agent 2'-fluoro-5-methyl-1-β-D-arabinofuranosyluracil (FMAU) with carbon-11 for use in in vivo imaging. 187*th National Meeting of the American Chemical Society*, St. Louis, Mo., April 8–13] with some modifications [Alauddin M. M., Conti P. S., Ravert, H. T., and Dannals R F. (1993b) Synthesis of high specific activity [$^{11}$C-methyl]-thymidine for in vivo imaging by positron emission tomography. 19*th American Chemical Society Western Regional Meeting*, Pasadena, Calif., October 19–24; Alauddin M. M. and Conti P. S. (1994) Selective alkylation of pyrimidyl dianions II: Synthesis, characterization and comparative reactivity of 3',5'-o-bis tetrahydropyranyl, trimethylsilyl, and t-butyldimethylsilyl derivatives of 5-bromo-deoxyuridine. *Tetrahedron* 50, 1699–1706]. The synthesis is illustrated in FIG. 1.

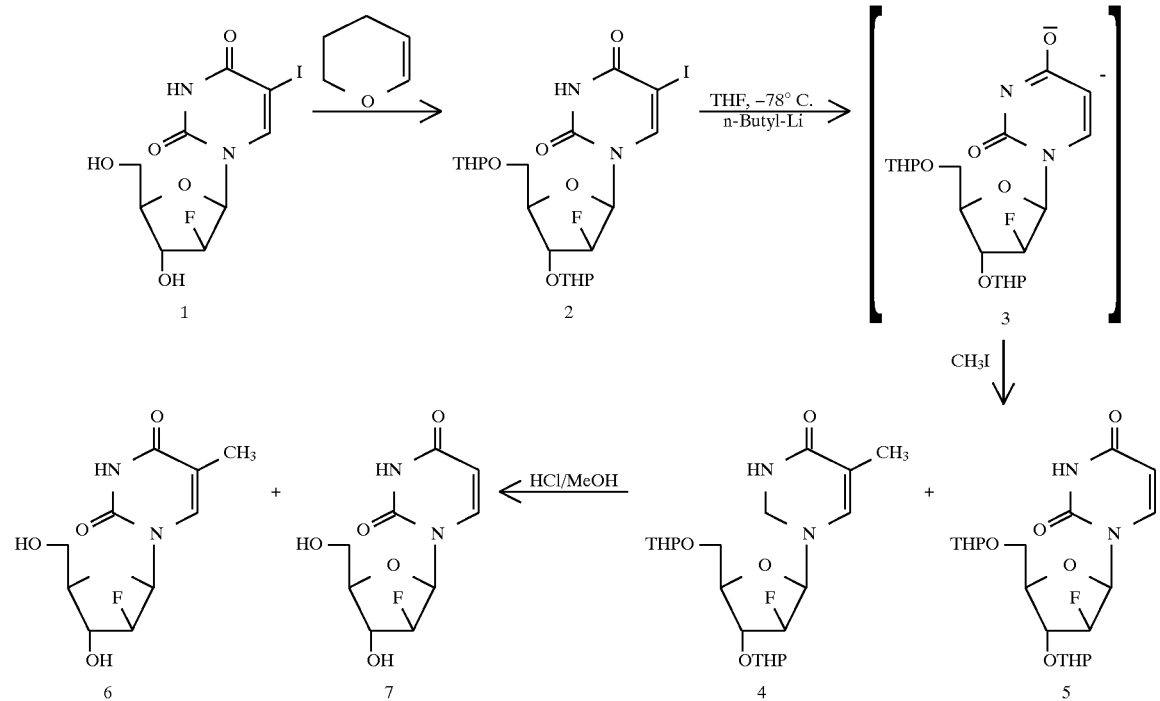

Scheme 1

After purification by flash chromatography compound 2 could be stored at room temperature for at least 10 months under anhydrous conditions. Its melting point was broad due to the fact that a mixture of four diastereomers were probably present. Treatment of compound 2 with n-butyllithium (2.5 equivalent) produced the dianion 3 in situ which was treated with either unlabeled or [$^{11}$C]-methyl iodide to produce the methylated product 4. The major by-product in the methylation reaction was the dehalogenated compound 5. The ratio of the desired product to the by-product was 43:57, as determined by $^1$HNMR integration of the C6 hydrogen. Deprotection of the tetrahydropyranyl ether produced the desired compound FMAU in 82% chemical yield.

In the radiolabeling experiments a slight modification was made. Briefly, a V-vial was used as reaction vessel instead of the round bottom flask used in standard preparations. The thick glass of the V-vials required additional time to warm the reaction mixture to room temperature (5 minutes instead of ~1 minute in the case of regular flask). The V-vial containing the in situ generated dianion was connected in series to the [$^{11}$C]-methyl iodide apparatus, so that the generated [$^{11}$C]-methyl iodide could be trapped directly and without delay in the reaction vial.

[11}C]-Methyl iodide was prepared from [$^{11}$C] $CO_2$ by a known procedure [Marazano C., Maziere M., Berger G, and Comar D. (1977) Synthesis of methyl iodide [$^{11}$C] and formaldehyde [$^{11}$C]. *Int. J. Appl. Rad. Isot.* 28: 49–52]. Using this procedure approximately 300–325 mCi of $^{11}$C-methyl iodide are produced routinely for synthetic work. At this level of $^{11}$C-methyl iodide, 10–62 mCi of [$^{11}$C]-FMAU could be produced routinely with radiochemical yields as high as 53% (based on starting [$^{11}$C]-methyl iodide) in 30–35 minutes from the end of bombardment. Radiochemical purity of [$^{11}$C]-FMAU was routinely >99% with specific activity up to 100 Ci/mmole. The major by-product of the reaction was the dehalogenated compound FAU. The labeled FMAU could be separated from FAU by HPLC on a reverse phase column using 10% acetonitrile in water as eluent. Analysis by HPLC gave peak a ($t_r$=3.6 min.) which co-elutes with an authentic sample of FAU. The second peak b along with a radioactive peak ($t_r$=5.9 min.) elutes at the same retention time as the authentic sample of FMAU. The desired product could be separated and easily isolated from other radioactive impurities.

The imaging agent of the present invention is used in a manner well known in the art for analogous compounds. In general, up to 20–25 mCi of radiolabeled material in physiological saline solution or equivalent vehicle is administered intravenously to a human or animal subject prior to imaging or probe studies. Data collection following administration may involve dynamic or static techniques with a variety of imaging devices, including PET cameras, gamma or SPECT (single photon emission computed tomography) cameras with either high energy collimators or coincidence detection capabilities, and probe devices designed to measure radioactive counts over specific regions of interest.

The invention may be better understood with reference to the accompanying example, which is intended for purposes of illustration only and should not be construed as in any sense limiting the scope of the invention as defined in the claims appended hereto.

EXAMPLE

2'-Fluoro-5-iodo-1-β-D-arabinofuranosyluracil (FIAU), 2'-fluoro-5-methyl-1-β-D-arabinofuranosyluracil (FMAU), and 2'-fluoro-1-β-D-arabinofuranosyl-uracil (FAU) were prepared according to published procedures [Watanabe K. A., Reichman U., Hirota K., et al. (1979) Nucleosides. 110. Synthesis and anitherpes virus activity of some 2'-fluoro-2'-deoxyarabinofuranosylpyrimidine nucleosides. *J. Med. Chem.* 22, 21–24]. p-Toluenesulfonic acid, 2,3-dihydropyran, and n-butyllithium were purchased from Aldrich. Flash chromatography was performed using silica gel 60 (E. M. Science) and HPLC grade solvents. Thin layer chromatography (TLC) was performed on pre-coated Kieselgel 60 F254 (Merck) glass plates. Melting points were determined on a capillary melting point apparatus and are uncorrected. $^1$HNMR studies were performed on a Bruker AMX300 spectrometer using tetramethylsilane as internal reference, unless otherwise specified. Mass spectra were obtained on a Finnigan 4000 mass spectrometer using ammonia chemical ionization technique unless otherwise specified, and m/z are reported only on the major peaks with relative intensity in the parenthesis. High performance liquid chromatography (HPLC) was performed on a Waters HPLC single pump isocratic system equipped with a computer (Macintosh), a UV detector (ISCO) at 254 nm, a radioactive detector (Technical Associates), and a semipreparative reverse phase $C_{18}$ column (Econosil, 10 micron, 250 mm×10 mm; Alltech). A solvent system of 10% acetonitrile in water was used as mobile phase.

For preparation of [$^{11}$C]-methyl iodide, [$^{11}$C]-$CO_2$ was produced by the reaction $^{14}$N (p, α) $^{11}$C in a RDS-112 Siemens 11 MeV cyclotron following a known procedure [Marazano et al., 1977, supra]. Briefly, [$^{11}$C]-$CO_2$ was bubbled through a solution of $LiAlH_4$ in THF (~300 μL, 8–10 mg/mL) under argon. The solvent was evaporated, and the residue was treated with HI (~0.5 mL). The reaction mixture was heated under reflux for 2 minutes. The [$^{11}$C]-methyl iodide produced was passed through columns of $P_2O_5$/NaOH, and finally bubbled through the pre-cooled solution of the dianion 3 in THF at −78° C.

For preparation of 3',5'-O-bis-(tetrahydropyranyl)-2'-fluoro-5-iodo-1-β-D-arabino-furanosyluracil 2,2'-Fluoro-5-iodo-1-β-D-arabinofuranosyluracil (FIAU) (71 mg, 0.19 mmol) was dissolved in dry THF (2 mL). p-Toluenesulfonic acid (catalytic amount) was added to the reaction flask followed by addition of 2,3-dihydropyran (0.242 ml, 2.8 mmol). The reaction mixture was stirred at room temperature for 2 h, at which time TLC showed no remaining starting material. The reaction was quenched by adding 2 drops of triethylamine. The solvent was evaporated, and the crude product was purified by flash chromatography using a silica gel column and 25% acetone in hexane as eluent. White solid, 96 mg of compound was obtained as a diastereomeric mixture in 93% yield. M.P. 65°–76° C. $^1$HNMR (CDCl$^3$): 8.748 (bs, 1H, NH), 8.019-7.974 (s, 1H, C$_6$H), 6.260-6.149 (dd, 1H, 1'H), 5.240 and 5.066 (2dd, 1H, 2'H, J FH=51.24 Hz, J HH=2.7 Hz), 4.805-4.726 (m, 2H), 4.255-3.565 (m, 9H), 1.834-1.570 (m, 11H). MS:558 (M+NH$_4$,4), 541 (M+1,2), 474 (21), 415 (16), 348 (62), 331 (100), 264 (35), 118 (24). Exact mass calculated for 2:540.0768; found: 540.0782 by isobutane chemical ionization MS.

For preparation of 3',5'-O-bis-(tetrahydropyranyl)-2'-fluoro-5-methyl- 1-β-D-arabinofuranosyluracil (4), 3',5'-O-Bis-(tetrahydropyranyl)-2'-fluoro-1-β-D-arabinofuranosyluracil (20 mg, 0.037 mmol) was dissolved in dry THF (1 mL) under argon and cooled to −78° C. n-Butyllithium (1.6M soln in hexane, 0.06 mL, 0.092 mmol) was injected into the cold solution, and the reaction mixture was stirred for 30 seconds. Methyl iodide (0.010 mL, 0.16 mmol) was injected into the reaction mixture, stirred for one minute, after which the cold bath was removed. By 2 minutes following addition of methyl iodide, no starting material was identified on TLC. The reaction was quenched with 0.10 mL saturated ammonium chloride solution and warmed to room temperature. Ethyl acetate (7 mL) was added to the reaction mixture, and the resulting solution was washed first with water (2×8 mL) and then with brine (1×5 mL). The aqueous phase was back extracted with ethyl acetate (1×8 mL). The combined organic phase was dried ($Na_2SO_4$) and evaporated to produce 16 mg of crude product. $^1$HNMR of this crude product showed a mixture of two compounds in the ratio 43:57 obtained by integration of the $C_6$ protons. The crude product was chromatographed using silica gel column and 20% acetone in hexane as eluent to produce 4 mg (25% yield) of the desired product. $^1$HNMR ($CDCl_3$):8.217 (bs, 1H, NH), 7.408 and 7.373 (2s, 1H, $C_6$H), 6.260-6.181 (dd, 1H, 1'H), 5.209 and 5.031 (2d, 1H, 2'H, J FH=52.8 Hz), 4.802-4.711 (m, 2H), 4.486-3.543 (m, 9H), 1.918 (s, 3H, $CH_3$), 1.790-1.573 (m, 11H). MS: 429 (M+1, 11), 362 (19), 345 (100), 261 (20), 118 (7). 3',5'-O-bis-(tetrahydropyranyl)-2'-fluoro-l1-β-D-arabinofuranosyluracil (5) was isolated as a by-product from the alkylation of the THP-protected FIAU described above. It gave acceptable spectra.

For preparation of 2'-fluoro-5-methyl-1-β-D-arabinofuranosyluracil (FMAU 6), }3',5'-O-Bis-(tetrahydropyranyl)-5-methyl-1-β-D-arabinofuranosyluracil (4 mg, 0.0093 mmol) was dissolved in methanol (1 mL) and three drops of methanol/conc. HCl (9:2) were added. The reaction mixture was refluxed for 3 minutes, when TLC showed no starting material remaining. The solvent was evaporated, the residue was washed with hexane and the washing was discarded. After evaporating off the residual solvent, 2 mg of the desired product was obtained in 82% yield. $^1$HNMR ($D_2O$): 7.656 (s, 1H, $C_6$H), 6.265 (dd, 1H, 1'H, J FH =16.86 Hz, J HH =4 Hz), 5.200 (dt, 1H, 2'H, J FH=51.6 Hz, J HH =3Hz), 4.431 (dt, 1H, 3'H, J FH=19.7 Hz, J HH=2.8 Hz), 4.029 (q, 1H, 4'H, J =3.7 Hz), 3.959 -3.823 (m, 2H, 5'H), 1.894 (s, 3H, $CH_3$). MS (FAB): 261 (M+1).

Preparation of 2'-fluoro-5-[$^{11}$C-methyl]-1-β-D-arabinofuranosyluracil ([$^{11}$C]-FMAU) was carried out as follows. 3',5'-o-Bis-(tetrahydropyranyl)-2'-fluoro-1-β-D-arabinofuranosyluracil 2 (10 mg, 0.0185 mmol) was dissolved in dry THF (0.5 mL) in a V-vial under argon and cooled to −78° C. n-Butyllithium (1.6M soln in hexane, 0.035 mL, 0.046 mmol) was injected into the cold solution. [$^{11}$C]-Methyl iodide was bubbled into the reaction mixture for 2 minutes. Trapped activity was measured in a dose calibrator (Capintec). The reaction mixture was warmed to room temperature followed by addition of 2M HCl in methanol (120 μL). The mixture was heated to reflux for 3 minutes in a heating block at 110° C. The residual solvent was evaporated with argon for 1 minute. After cooling, the reaction mixture was neutralized with 2M NaOH solution (80 μL). The crude product was diluted with HPLC solvent (1 mL), and injected onto the semipreparative HPLC column for purification. The desired product was isolated from the appropriate fraction. Quality control was performed by injecting an aliquot onto the HPLC column.

HPLC analysis of [$^{11}$C]-FMAU and FAU was carried out as follows. FAU was eluted at 6.2 minutes and [$^{11}$C]-FMAU was eluted at 9.7 minutes at a flow rate of 4 mL/minute. Isolated product was re-analyzed on the same column using a flow rate of 6 mL/min ($t_r$=5.9 min).

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A composition of matter for in vivo diagnostic imaging of cellular proliferation comprising:

(a) an imaging agent in dosage unit form, wherein the unit dose of the the imaging agent comprises a non-toxic amount of 2'-fluoro-5-[$^{11}$C]-methyl-1-β-D-arabinofuranosyluracil capable of localizing in proliferating cells and being detected in vivo; and (b) a physiologically acceptable carrier or adjuvant.

2. A composition according to claim 1, comprising up to 25 mCi of [$^{11}$C] per unit dose.

3. A method of imaging proliferating cells in vivo, comprising the steps of:

(a) administering a unit dose of an imaging agent, wherein the unit dose of the imaging agent comprises a non-toxic amount of 2'-fluoro-5-[$^{11}$C]-methyl-1β-D-arabinofuranosyluracil; and (b) detecting said imaging agent in vivo localized in proliferating cells.

4. A method according to claim 3, wherein the imaging agent is administered in a unit dose comprising up to 25 mCi of [$^{11}$C].

5. A composition of matter according to claim 1, the 2'-fluoro-5-[$^{11}$C]-methyl-1-β-D-arabinofuranosyluracil having a specific activity of about 50 to about 100 Ci/mmol.

6. A method according to claim 3, the 2'-fluoro-5-[$^{11}$C]-methyl-1-β-D-arabinofuranosyluracil having a specific activity of about 50 to about 100 Ci/mmol.

* * * * *